(12) United States Patent
Quapp et al.

(10) Patent No.: US 7,816,415 B2
(45) Date of Patent: Oct. 19, 2010

(54) METHOD AND APPARATUS FOR SYNTHESIZING HYDROCARBONS USING SONIC MIXING AND SOLID CATALYSTS

(75) Inventors: William J. Quapp, Idaho Falls, ID (US); Jeffrey E. Surma, Richland, WA (US); James A. Batdorf, Kennewick, WA (US)

(73) Assignee: InEnTec LLC, Bend, OR (US)

( * ) Notice: Subject to any disclaimer, the term of this patent is extended or adjusted under 35 U.S.C. 154(b) by 293 days.

(21) Appl. No.: 11/879,585

(22) Filed: Jul. 17, 2007

(65) Prior Publication Data

US 2009/0023821 A1    Jan. 22, 2009

(51) Int. Cl.
*C07C 27/00*    (2006.01)

(52) U.S. Cl. .................. 518/700; 518/714; 518/715; 518/717

(58) Field of Classification Search .......... 518/700, 518/714, 715, 717
See application file for complete search history.

(56) References Cited

U.S. PATENT DOCUMENTS

| | | | |
|---|---|---|---|
| 2,091,414 A | 8/1937 | Newport et al. |
| 2,353,492 A | 7/1944 | O'Connor |
| 2,636,719 A | 4/1953 | O'Connor |
| 3,162,910 A | 12/1964 | Behnke et al. |
| 3,498,384 A | 3/1970 | Ogura |
| 3,583,246 A | 6/1971 | Stahle et al. |
| 3,767,168 A | 10/1973 | Dupre et al. |
| 4,619,532 A | 10/1986 | Schmidt, III |
| 4,972,930 A | 11/1990 | Davis |
| 5,666,891 A | 9/1997 | Titus et al. |
| 5,756,957 A | 5/1998 | Titus et al. |
| 5,785,923 A | 7/1998 | Surma et al. |
| 5,798,497 A | 8/1998 | Titus et al. |
| 5,811,752 A | 9/1998 | Titus et al. |
| 5,847,353 A | 12/1998 | Titus et al. |
| 5,908,564 A | 6/1999 | Titus et al. |
| 5,979,242 A | 11/1999 | Hobbs |
| 6,018,471 A | 1/2000 | Titus et al. |
| 6,018,542 A | 1/2000 | Berger |
| 6,037,560 A | 3/2000 | Titus et al. |
| 6,049,560 A | 4/2000 | Freeman |
| 6,066,825 A | 5/2000 | Titus et al. |
| 6,127,645 A | 10/2000 | Titus et al. |
| 6,160,238 A | 12/2000 | Titus et al. |
| 6,213,630 B1 | 4/2001 | Kossmann |
| 6,215,678 B1 | 4/2001 | Titus et al. |
| 6,250,792 B1 | 6/2001 | Krush et al. |
| 6,263,750 B1 | 7/2001 | Maurer et al. |
| 6,371,711 B1 | 4/2002 | Berger |
| 6,486,219 B1 * | 11/2002 | Janda et al. ................. 518/706 |
| 6,570,906 B2 | 5/2003 | Titus |
| 6,576,210 B2 | 6/2003 | Surma |
| 6,579,002 B1 | 6/2003 | Bartick et al. |
| 6,630,113 B1 | 10/2003 | Surma |
| 6,737,604 B2 | 5/2004 | Surma et al. |
| 6,805,107 B2 | 10/2004 | Vinyard |
| 7,115,670 B2 * | 10/2006 | Hensman et al. ............ 518/712 |
| 7,188,993 B1 | 3/2007 | Howe et al. |

OTHER PUBLICATIONS

Chemical, Low-Frequency Sonic Mixing Technology, Office of Industrial Technology, US Department of Energy, 2001.*
U.S. Appl. No. 11/177,152, filed Jul. 6, 2005.
U.S. Appl. No. 11/432,826, filed May 12, 2006.

* cited by examiner

*Primary Examiner*—Jafar Parsa
(74) *Attorney, Agent, or Firm*—Douglas E. McKinley, Jr.

(57) ABSTRACT

Gasses containing carbon monoxide and hydrogen are converted into hydrocarbons using a reactor vessel having a liquid, a catalyst dispersed in the liquid, and a sonic mixing system interfaced with the reactor vessel. The sonic mixing system is used to agitate the mixture. In combination with the catalysts, the agitation increases reaction kinetics, thereby promoting chemical reactions used to efficiently convert gasses containing carbon monoxide and hydrogen into hydrocarbons.

5 Claims, 1 Drawing Sheet

METHOD AND APPARATUS FOR SYNTHESIZING HYDROCARBONS USING SONIC MIXING AND SOLID CATALYSTS

TECHNICAL FIELD

This invention relates to catalytic chemistry. More specifically, this invention relates to Fischer-Tropsch or similar processes involving catalyzed chemical reactions in which gasses containing carbon monoxide and hydrogen are converted into liquid hydrocarbons of various forms. The invention uses a combination of sonic mixing and solid catalysts to produce alcohols or synthetic petroleum substitutes for a variety of uses, including but not limited to as synthetic lubricants, or as synthetic fuels.

BACKGROUND OF THE INVENTION

Concerns relating to national and economic security have created a desire within the United States to find a replacement for energy resources imported from foreign countries. Among the many so-called "alternative fuels" that have been proposed as a replacement for imported oil are methanol, ethanol and biodiesel. Crops such as corn are routinely converted into ethanol, and soybeans, rapeseed, and other vegetable oils into bio-diesel fuel. The production of bio-diesel from animal and vegetable oils is also commonly performed, using a chemical conversion by reacting the oils with methanol. These market forces have greatly increased the demand for alternate sources of methanol, preferably from renewable and domestic sources. One drawback associated with these methods is the costs associated with producing the agricultural feedstocks.

Simultaneously with these efforts, the desire to provide a safe and reliable waste disposal method has led to the development of systems that generate usable energy or chemical products from hazardous and municipal solid wastes. These systems are also being developed to use waste agricultural biomass materials such as corn stover, forest harvesting residues, forest timber, and crops grown specifically for the biomass content such as switch grass. For example, Integrated Environmental Technologies LLC, the assignee of the present invention, markets systems that convert organic waste materials into a hydrogen rich synthesis gas.

These systems are described in the following US patents and pending US patent applications, the entire contents of which are herein incorporated into this disclosure in their entirety by this reference:

U.S. Pat. No. 5,666,891 Arc Plasma-Melter Electro Conversion System for Waste Treatment and Resource Recovery—Issued Sep. 16, 1997, U.S. Pat. No. 5,756,957 Tunable Molten Oxide Pool Assisted Plasma Melter Vitrification System—Issued May 26, 1998, U.S. Pat. No. 5,785,923 Apparatus for Continuous Feed Material Melting—Issued Jul. 28, 1998, U.S. Pat. No. 5,798,497 Tunable, Self-Powered Integrated Arc Plasma-Melter Vitrification System for Waste Treatment and Resource Recovery—Issued Aug. 25, 1998, U.S. Pat. No. 5,811,752 Enhanced Tunable Plasma-Melter Vitrification Systems—Issued Sep. 22, 1998, U.S. Pat. No. 5,847,353 Methods and Apparatus for Low $NO_x$ Emissions during the Production of Electricity from Waste Treatment Systems—Issued Dec. 8, 1998, U.S. Pat. No. 5,908,564 Tunable, Self-powered Arc Plasma-melter Electro Conversion System for Waste Treatment and Resource Recovery—Issued Jun. 1, 1999, U.S. Pat. No. 6,018,471 Methods and Apparatus for Treating Waste—Issued Jan. 25, 2000, U.S. Pat. No. 6,037,560 Enhanced Tunable Plasma-Melter Vitrification Systems—Issued Mar. 14, 2000, U.S. Pat. No. 6,215,678 Arc Plasma Joule Heated Melter System for Waste Treatment and Resource Recovery—Issued Apr. 10, 2001, U.S. Pat. No. 6,127,645 Tunable, Self-powered Arc Plasma-melter Electro Conversion System for Waste Treatment and Resource Recovery—Issued Oct. 3, 2000, U.S. Pat. No. 6,160,238 Tunable Molten Oxide Pool Assisted Plasma Melter Vitrification System—Issued Dec. 12, 2000, U.S. Pat. No. 6,066,825 Methods and Apparatus for Low $NO_x$ Emissions during the Production of Electricity from Waste Treatment Systems—Issued May 23, 2000, U.S. Pat. No. 6,576,210 Method for Complete Destruction of Carbon in High Temperature Plasma Waste Treatment Systems—Issued Jun. 10, 2003, U.S. Pat. No. 6,630,113 Methods and Apparatus for Treating Waste—Issued Oct. 7, 2003, U.S. Pat. No. 6,018,542 Sealed Electrode Feeding Assembly—Issued Jan. 25, 2000, U.S. Pat. No. 6,049,560 Inductively Heated Side Drain for High Temperature Molten Materials—Issued Oct. 11, 2000, U.S. Pat. No. 6,371,711 Valveless Continuous Atmospherically Isolated Container Feeding Assembly—Issued Apr. 16, 2002, U.S. Pat. No. 6,737,604 Symbiotic Solid Waste Gaseous Waste Conversion System for High Efficiency Electricity Production—Issued May 18, 2004, U.S. Pat. No. 6,570,906 Arc Furnace with DC Arc and AC Joule Heating—Issued May 27, 2003, U.S. Pat. No. 6,805,107 Dual Fuel Source Carburetor Method—Issued Oct. 19, 2004, Ser. No. 11/177,152 Method For Enhancing The Operation Of Electrical Power Plants and Energy Storage—Filed Jul. 6, 2005.

These waste treatment systems have proven to be effective in converting waste and biomass products to useful energy in the form of synthesis gas, and the synthesis gas produced by these and similar waste treatment systems can be converted into liquid fuels using known techniques involving catalytic reactors that operate at high pressure and elevated temperature. However, there exists a need to improve the gas to liquids conversion process, and specifically to improve the conversion efficiency, the yield per ton of syngas, and the specificity of the intended product or combinations thereof.

Among the commercial methods and apparatus that are relevant to this disclosure are sonic mixing systems. Sonic mixing systems are commercially available. One such system manufactured by Resodyn Corporation of Butte, Mont., is disclosed in U.S. Pat. No. 7,188,993, which describes an apparatus and method for resonant-vibratory mixing that describes a three-mass system having a structure that is capable of achieving low-frequencies of 10 to 1000 Hertz (Hz), high accelerations of 2 to 75 accelerations equal to that caused by gravity (g's) and large displacement amplitudes of 0.01 to 0.5 inches.

Other systems are described in the following US Patents, the entire contents of which are herein incorporated into this disclosure in their entirety by this reference. U.S. Pat. No. 2,091,414 discloses an apparatus for effecting vibration. U.S. Pat. No. 3,162,910 discloses an apparatus for shaking out foundry flasks. U.S. Pat. Nos. 2,353,492 and 2,636,719 disclose devices that provide for the vibrational compaction of dry materials and for the feeding of material via a vibratory conveyance. U.S. Pat. No. 6,213,630 claims electronic control of motors for the purpose of vibrational control of a compaction device. U.S. Pat. No. 3,498,384 discloses a vibratory impact device. U.S. Pat. No. 3,583,246 discloses a vibration device driven by at least one imbalance generator. U.S. Pat. No. 3,767,168 discloses a mechanical agitation apparatus. U.S. Pat. No. 4,619,532 discloses a shaker for paint containers. U.S. Pat. No. 4,972,930 discloses a dynamically adjustable rotary unbalance shaker. U.S. Pat. No. 5,979,242 discloses a multi-level vibration test system having controllable vibration attributes. U.S. Pat. No. 6,250,792 discloses an integrated vibratory adapter device. U.S. Pat. No. 6,263,750 discloses a device for generating directed vibrations. U.S. Pat. No. 6,579,002 discloses a broad-range large-load fast-oscillating high-performance reciprocating programmable laboratory shaker.

Thus, there exists a need for new methods and apparatus to convert organic waste streams into methanol, ethanol and other liquid products. There is a further need for new methods and apparatus to convert gasses having hydrogen and carbon dioxide into methanol and other liquid products. The present invention addresses those needs.

SUMMARY OF THE INVENTION

One object of this invention is to provide a method for forming hydrocarbons from gasses containing carbon monoxide and hydrogen. Another object of this invention is to provide a method of accelerating reaction kinetics in liquid phase catalytic reactors through the addition of solid catalysts. Yet another object of this invention is to provide a liquid phase reactor with a solid catalyst that can form hydrocarbons from gasses containing carbon monoxide and hydrogen. It is yet another object of the present invention to provide a method and apparatus that can form hydrocarbons from gasses containing carbon monoxide and hydrogen at sufficiently high rates to provide large volumes of the hydrocarbons.

These and other objects of the present invention are accomplished by providing a method and apparatus for synthesizing hydrocarbons from gasses containing carbon monoxide and hydrogen. The present invention provides a reactor vessel. Within said reactor vessel is a liquid. Dispersed in said liquid is a catalyst. A gas containing carbon monoxide and hydrogen is introduced into the liquid in the reactor vessel. A sonic mixing system interfaced with the reactor vessel is used to agitate the mixture, thereby enhancing at least one chemical reaction converting the carbon monoxide and hydrogen into at least one hydrocarbon. It is widely know that sonic mixing can cause intense breakdown of the boundary layer thickness between solids and liquids by the formation and collapse of bubbles. Such enhanced mixing at the catalyst surface will enhance the mass transport of reacting products to the surface and the removal of reaction products from the surface. With this enhanced mixing caused by the sonic mixing, enhanced reaction rates are achieved, and thus, enhanced process efficiency is achieved.

It is preferred that the catalyst is selected from the group Fe, FeCo, Zn/Cr, Cu/Zn/Cr, Cu/Zn, Cu/Zn/$Al_2O_3$, Cu/Co, Cu/Co/$Al_2O_3$, Ni, Mo, $MoS_2$, Co/$MoS_2$, $ThO_2$, W, and $Zr_2O_3$, and combinations thereof. The catalysts may be supported on a substrate or unsupported. Suitable substrates include, but are not limited to, carbon, Al2O3, SiO2, and Zr2O3. The substrates may be modified or unmodified with a dopant. Suitable dopants include, but are not limited to alkali metals, alkaline earth metals, or precious metals and combinations thereof.

It is preferred that the hydrocarbons formed by the method and apparatus of the present invention are selected from the group methanol, ethanol, higher alcohols, diesel, gasoline, dimethyl ether, and combinations thereof or combinations that include such hydrocarbons in addition to other substances.

It is preferred that the sonic mixing system of the present invention be operated between 10 and 1000 Hertz.

To promote a simple separation of the hydrocarbons formed by the method and apparatus of the present invention and the catalyst bearing liquid phase in the reactor vessel, it is preferred that the hydrocarbons formed by the method and apparatus of the present invention exist as gasses under the temperature and pressure conditions of the reactor vessel and it is preferred that the catalyst bearing liquid phase be a liquid under the temperature and pressure conditions of the reactor vessel. Suitable temperatures for the reactor vessel range from about 100° C. to about 450° C. Suitable pressures for the reactor vessel range from about 15 bar to about 150 bar. Preferred hydrocarbons formed by the method and apparatus of the present invention include, but are not limited to, methanol, ethanol, higher alcohols, diesel, gasoline, dimethyl ether, and combinations thereof. Suitable liquids for the catalyst bearing liquid phase in the reactor vessel include, but are not limited to, mineral oil and similar hydrocarbons and paraffins.

DESCRIPTION OF THE DRAWINGS

The following detailed description of the embodiments of the invention will be more readily understood when taken in conjunction with the following drawing, wherein.

DETAILED DESCRIPTION OF THE PREFERRED EMBODIMENTS

Figure 1:
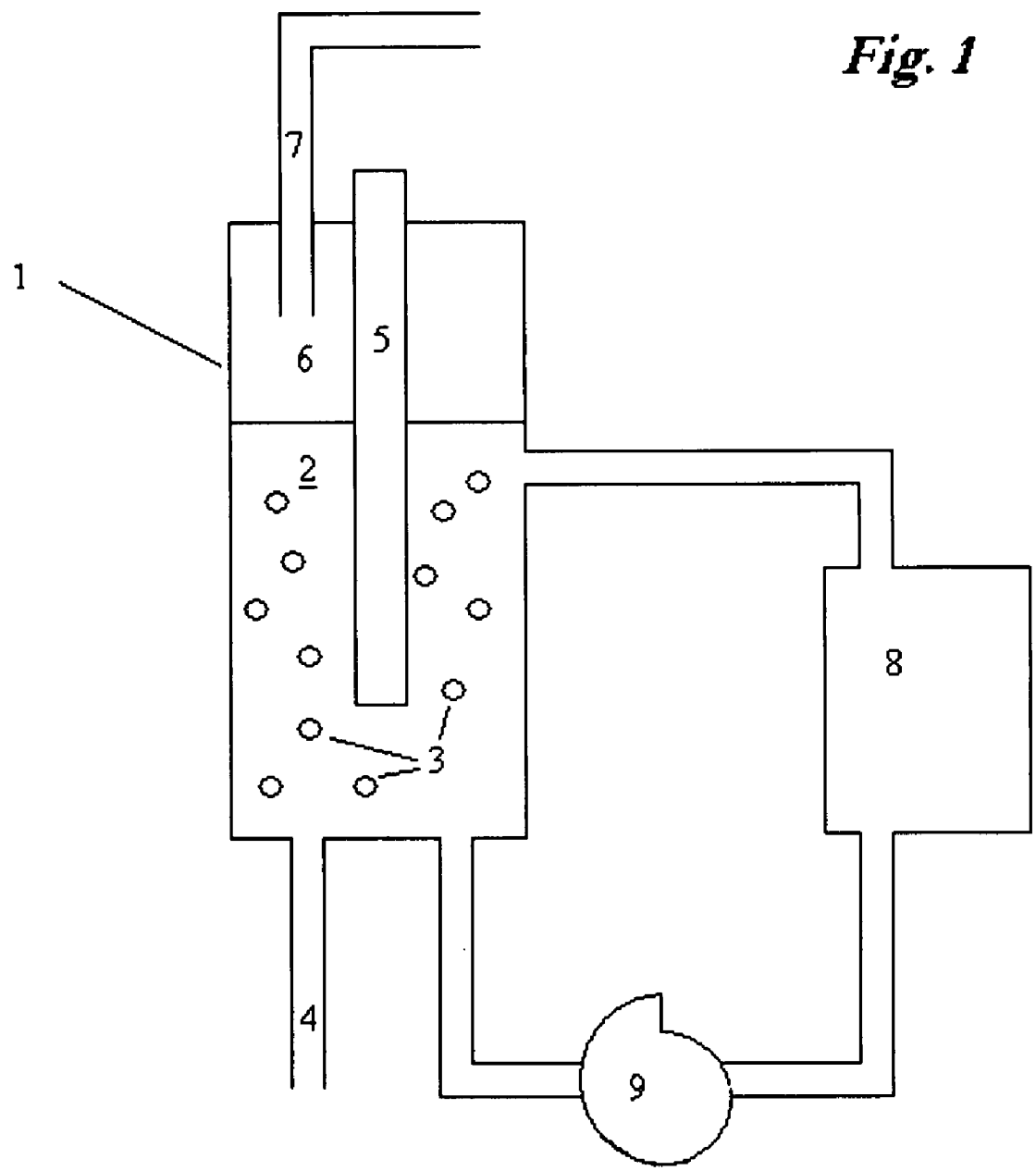
FIG. 1 is an illustration of the apparatus of the present invention.

For the purpose of promoting an understanding of the principles of the invention, reference will now be made to the embodiments illustrated in the drawing and specific language will be used to describe the same. It will nevertheless be understood that no limitations of the inventive scope is thereby intended, as the scope of this invention should be evaluated with reference to the claims appended hereto. Alterations and further modifications in the illustrated devices, and such further applications of the principles of the invention as illustrated herein are contemplated as would normally occur to one skilled in the art to which the invention relates.

As shown in FIG. 1, a reactor vessel 1 is provided having a liquid 2 therein, and a catalyst 3 dispersed throughout the liquid 2. An inlet 4 is provided to reactor vessel 1. Gasses containing carbon monoxide and hydrogen are introduced into reactor vessel 1 through inlet 4. Sonic mixing system 5 is interfaced with the reactor vessel 1.

Sonic mixing system 5 is used to agitate the mixture, thereby enhancing at least one chemical reaction converting the carbon monoxide and hydrogen into at least one hydrocarbon 6. Hydrocarbon 6 is then removed from liquid reactor vessel 1 through outlet port 7. In some applications, Liquid 2 and catalyst 3 are directed through an external heat exchanger 8 by pump 9. In this manner, the heat of the reactions forming hydrocarbons 6 is dissipated from liquid reactor vessel 1.

While the invention has been illustrated and described in detail in the drawing and foregoing description, the same is to be considered as illustrative and not restrictive in character. Only certain embodiments have been shown and described, and all changes, equivalents, and modifications that come within the spirit of the invention described herein are desired to be protected. Any experiments, experimental examples, or experimental results provided herein are intended to be illustrative of the present invention and should not be considered limiting or restrictive with regard to the invention scope. Further, any theory, mechanism of operation, proof, or finding stated herein is meant to further enhance understanding of the present invention and is not intended to limit the present invention in any way to such theory, mechanism of operation, proof, or finding.

Thus, the specifics of this description and the attached drawing should not be interpreted to limit the scope of this invention to the specifics thereof. Rather, the scope of this invention should be evaluated with reference to the claims appended hereto. In reading the claims it is intended that when words such as "a", "an", "at least one", and "at least a portion" are used there is no intention to limit the claims to only one item unless specifically stated to the contrary in the claims. Further, when the language "at least a portion" and/or "a portion" is used, the claims may include a portion and/or the entire items unless specifically stated to the contrary. Likewise, where the term "input" or "output" is used in connection with an electric device or fluid processing unit, it should be understood to comprehend singular or plural and one or more signal channels or fluid lines as appropriate in the context. Finally, all publications, patents, and patent applications cited in this specification are herein incorporated by reference to the extent not inconsistent with the present disclosure as if each were specifically and individually indicated to be incorporated by reference and set forth in its entirety herein.

We claim:

1. A method for synthesizing hydrocarbons from gasses containing carbon monoxide and hydrogen comprising the steps of:
   a. providing a reactor vessel,
   b. providing a sonic mixing system interfaced with said reactor vessel,
   c. providing a liquid in said reactor vessel,
   d. providing a catalyst dispersed within said liquid,
   e. directing a gas containing carbon monoxide and hydrogen into said liquid,
   f. agitating said mixture with said sonic mixing system, thereby enhancing at least one chemical reaction converting the carbon monoxide and hydrogen into at least one hydrocarbon, and
   g. maintaining the reactor vessel at a temperature and pressure such that the liquid in the reactor vessel is maintained as in a liquid phase and the hydrocarbons formed from the reaction of carbon monoxide and hydrogen into at least one hydrocarbon is maintained in a gas phase.

2. The method of claim 1 wherein the catalyst is selected from the group Fe, FeCo, Zn/Cr, Cu/Zn/Cr, Cu/Zn, Cu/Zn/$Al_2O_3$, Cu/Co, Cu/Co/$Al_2O_3$, Ni, Mo, $MoS_2$, Co/$MoS_2$, $ThO_2$, W, and $Zr_2O_3$, and combinations thereof, either supported or unsupported, wherein the support consists of carbon, $Al_2O_3$, $SiO_2$, $Zr_2O_3$, and combinations thereof, said support either modified or unmodified with a dopant, wherein the dopant is selected from the alkali metals, alkaline earth metals, or precious metals and combinations thereof.

3. The method of claim 1 wherein the hydrocarbons are selected from the group methanol, ethanol, higher alcohols, diesel, gasoline, dimethyl ether, and combinations thereof.

4. The method of claim 1 wherein the sonic mixing system is operated between 10 and 1000 Hertz.

5. The method of claim 1 wherein the liquid is selected as mineral oil.

* * * * *